United States Patent
Swanson

(10) Patent No.: US 6,942,661 B2
(45) Date of Patent: Sep. 13, 2005

(54) FLUID COOLED APPARATUS FOR SUPPORTING DIAGNOSTIC AND THERAPEUTIC ELEMENTS IN CONTACT WITH TISSUE

(75) Inventor: David K. Swanson, Campbell, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 09/761,981

(22) Filed: Jan. 17, 2001

(65) Prior Publication Data

US 2002/0026187 A1 Feb. 28, 2002

Related U.S. Application Data

(63) Continuation-in-part of application No. 09/652,099, filed on Aug. 30, 2000, now Pat. No. 6,579,288.

(51) Int. Cl.$^7$ .............................................. A61B 18/18
(52) U.S. Cl. .................................................... 606/41
(58) Field of Search ....................... 606/41, 42, 46–50; 607/116, 100–5

(56) References Cited

U.S. PATENT DOCUMENTS

| | | | |
|---|---|---|---|
| 4,326,529 A | 4/1982 | Doss et al. | |
| 5,085,657 A | 2/1992 | Ben-Simhon | |
| 5,281,213 A | 1/1994 | Milder et al. | |
| 5,292,320 A | 3/1994 | Brown et al. | |
| 5,334,193 A | 8/1994 | Nardella | |
| 5,348,554 A | 9/1994 | Imran | |
| 5,383,876 A | 1/1995 | Nardella | |
| 5,409,483 A | 4/1995 | Campbell et al. | |
| 5,443,470 A | 8/1995 | Stern et al. | |
| 5,496,271 A | 3/1996 | Burton et al. | |
| 5,505,730 A | 4/1996 | Edwards | |
| 5,569,241 A | 10/1996 | Edwards | |
| 5,569,242 A | 10/1996 | Lax | |
| 5,584,872 A | * 12/1996 | LaFontaine et al. | ........ 607/116 |
| 5,609,151 A | 3/1997 | Mulier | |
| 5,624,392 A | 4/1997 | Saab | |
| 5,630,837 A | 5/1997 | Crowley | |
| 5,676,693 A | 10/1997 | LaFontaine | |
| 5,683,366 A | 11/1997 | Eggers | |
| 5,688,267 A | * 11/1997 | Panescu et al. | ............... 606/31 |
| 5,697,536 A | 12/1997 | Eggers | |
| 5,697,882 A | 12/1997 | Eggers | |

(Continued)

FOREIGN PATENT DOCUMENTS

| | | |
|---|---|---|
| EP | 0856292 A1 | 8/1998 |
| EP | 1169972 A1 | 1/2002 |
| WO | WO 99/48421 | 9/1999 |
| WO | WO-00/56237 A2 | 9/2000 |

OTHER PUBLICATIONS

Claims as of Jan. 27, 2003, for U.S. Appl. No. 09/737,176.
U.S. Appl. No. 09/652,099, filed Aug. 30, 2000, Swanson et al.
Claims as of Oct. 6, 2002 for U.S. Appl. No. 09/652,099.
PCT Inv. to Pay Additional Fees & Partial Search dated Jan. 3, 2002 for PCT App. No. PCT/EP01/09182.
PCT Int. Search Report Dated Mar. 21, 2002 for PCT App. No. Ser. PCT/EP01/09182.

*Primary Examiner*—Michael Peffley
*Assistant Examiner*—Pete Vrettakos
(74) *Attorney, Agent, or Firm*—Henricks, Slavin & Holmes LLP

(57) ABSTRACT

Surgical methods and apparatus for positioning diagnostic an therapeutic elements on the epicardium or other organ surface. The apparatus includes a tissue cooling apparatus.

39 Claims, 13 Drawing Sheets

U.S. PATENT DOCUMENTS

| | | | |
|---|---|---|---|
| 5,697,927 A | | 12/1997 | Imran et al. |
| 5,785,706 A | * | 7/1998 | Bednarek ............... 606/41 |
| 5,792,140 A | * | 8/1998 | Tu et al. ............... 606/41 |
| 5,797,903 A | * | 8/1998 | Swanson et al. .......... 606/34 |
| 5,800,482 A | | 9/1998 | Pomeranz |
| 5,800,484 A | | 9/1998 | Gough |
| 5,833,688 A | | 11/1998 | Sieben et al. |
| 5,879,347 A | | 3/1999 | Saadat |
| 5,879,348 A | | 3/1999 | Owens |
| 5,891,134 A | * | 4/1999 | Goble et al. ............ 606/27 |
| 5,910,129 A | | 6/1999 | Koblish |
| 5,913,854 A | | 6/1999 | Maguire et al. |
| 5,938,659 A | | 8/1999 | Tu et al. |
| 5,951,546 A | | 9/1999 | Lorentzen |
| 5,957,922 A | | 9/1999 | Imran |
| 5,961,490 A | | 10/1999 | Adams |
| 5,961,513 A | | 10/1999 | Swanson |
| 6,002,968 A | | 12/1999 | Edwards |
| 6,012,457 A | | 1/2000 | Lesh |
| 6,015,407 A | | 1/2000 | Rieb et al. |
| 6,017,338 A | | 1/2000 | Brucket et al. |
| 6,024,740 A | | 2/2000 | Lesh |
| 6,032,077 A | | 2/2000 | Pomeranz |
| 6,036,697 A | | 3/2000 | DiCaprio |
| 6,048,329 A | | 4/2000 | Thompson et al. |
| 6,053,912 A | | 4/2000 | Panescu et al. |
| 6,053,937 A | | 4/2000 | Edwards et al. |
| 6,068,653 A | | 5/2000 | LaFontaine |
| 6,071,274 A | | 6/2000 | Thompson |
| 6,071,279 A | | 6/2000 | Whayne |
| 6,071,281 A | | 6/2000 | Burnside |
| 6,076,012 A | | 6/2000 | Swanson et al. |
| 6,117,101 A | | 9/2000 | Diederich |
| 6,164,283 A | | 12/2000 | Lesh |
| 6,168,594 B1 | | 1/2001 | LaFontaine |
| 6,241,727 B1 | | 6/2001 | Tu et al. |
| 6,258,087 B1 | | 7/2001 | Edwards et al. |
| 6,264,654 B1 | | 7/2001 | Swartz et al. |
| 6,270,493 B1 | | 8/2001 | Lalonde et al. |
| 6,277,115 B1 | * | 8/2001 | Saadat ............... 606/41 |
| 6,280,441 B1 | | 8/2001 | Ryan |
| 6,290,699 B1 | | 9/2001 | Hall et al. |
| 6,306,133 B1 | | 10/2001 | Tu et al. |
| 6,371,955 B1 | | 4/2002 | Fuimaono |
| 6,485,489 B2 | | 11/2002 | Teirstein et al. |
| 6,522,930 B1 | | 2/2003 | Schaer et al. |
| 6,579,288 B1 | | 6/2003 | Swanson et al. |
| 6,837,885 B2 | | 1/2005 | Koblish et al. |
| 2001/0007071 A1 | | 7/2001 | Koblish et al. |
| 2002/0128640 A1 | * | 9/2002 | Swanson ............... 606/32 |
| 2003/0069570 A1 | | 4/2003 | Witzel et al. |

\* cited by examiner

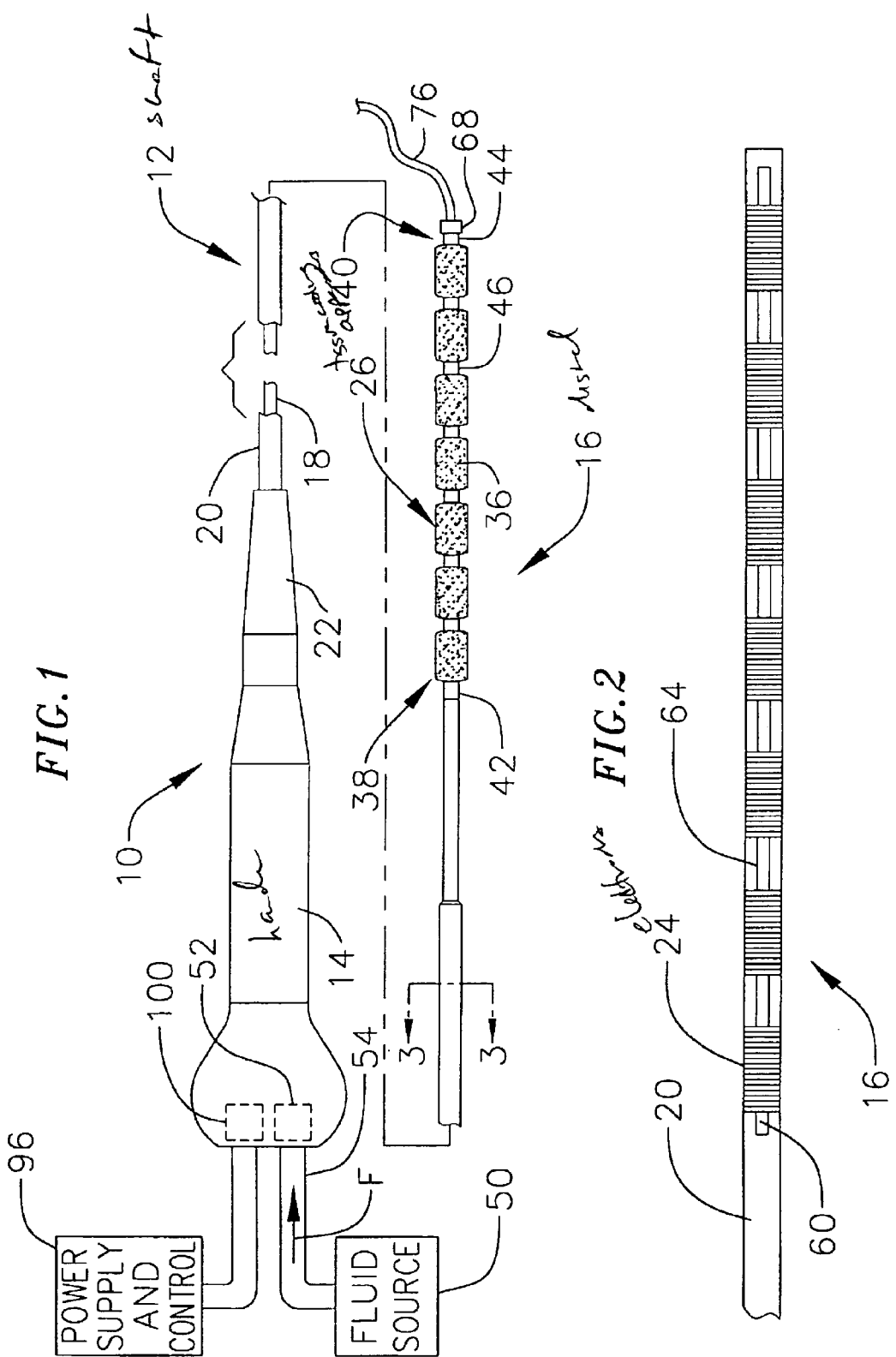

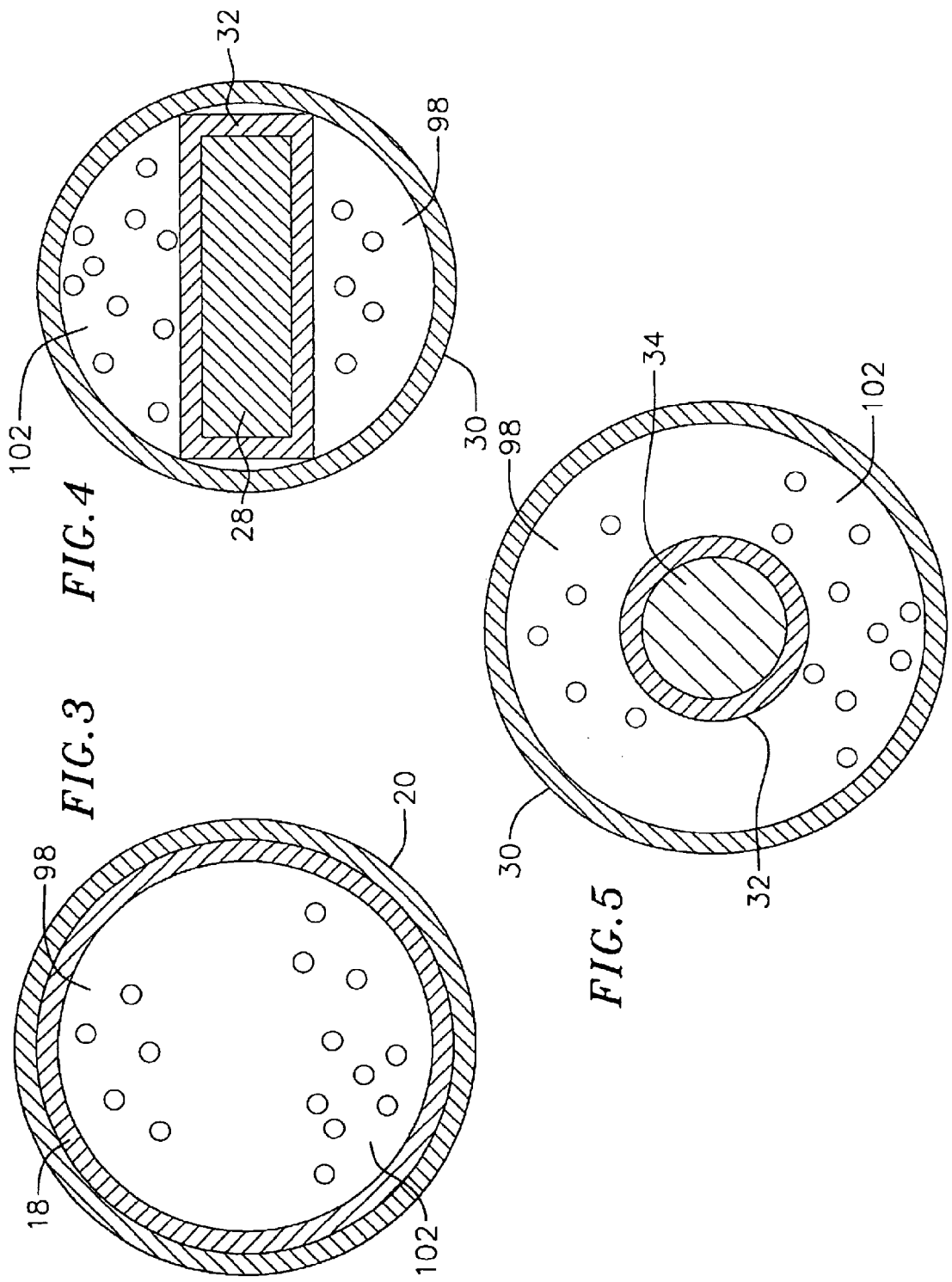

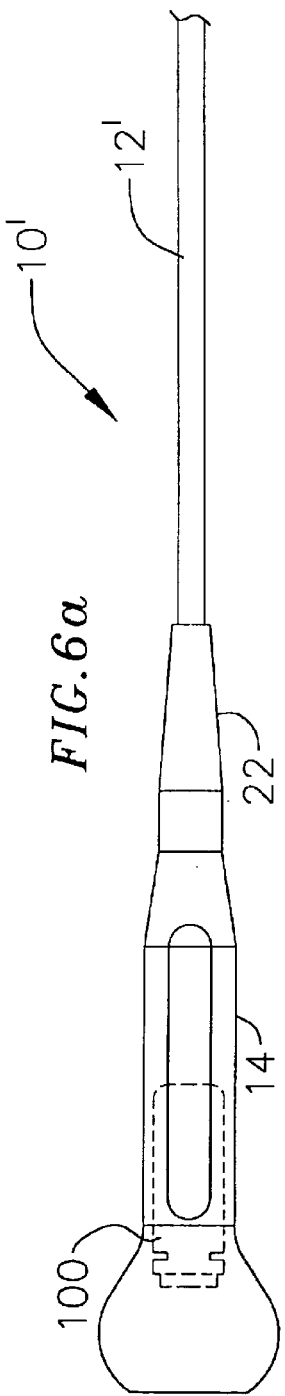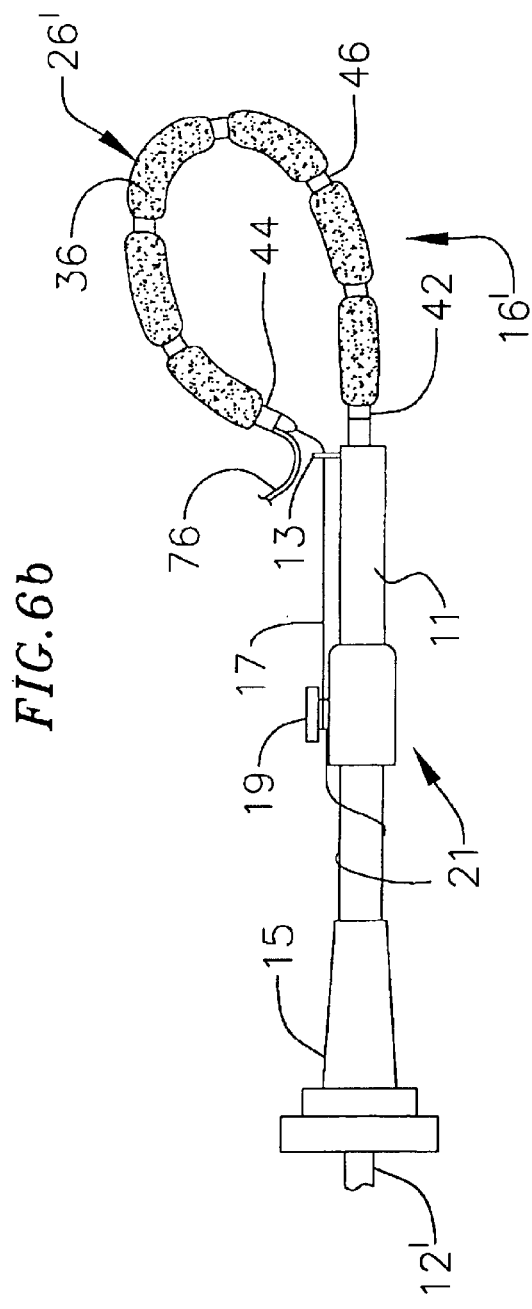
FIG.6a
FIG.6b

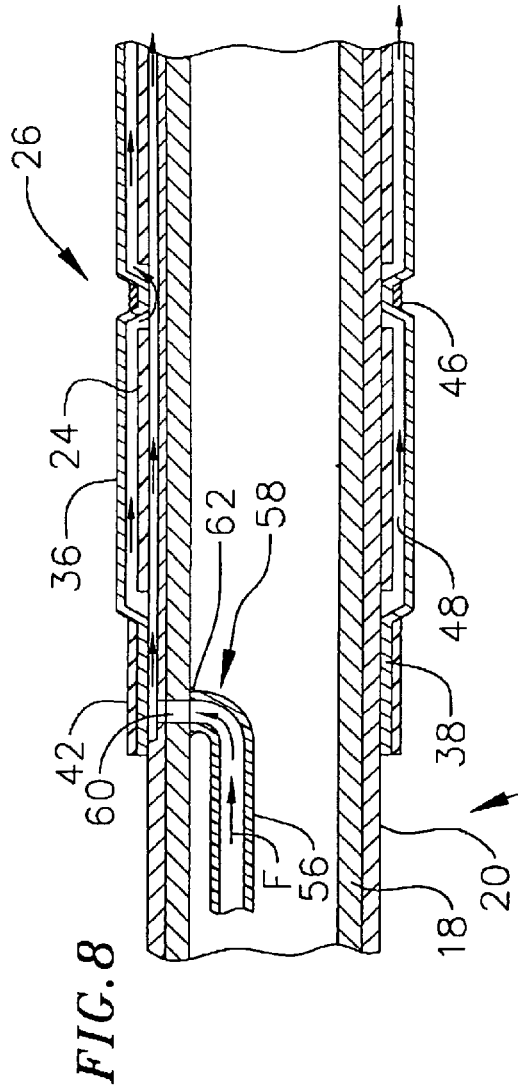
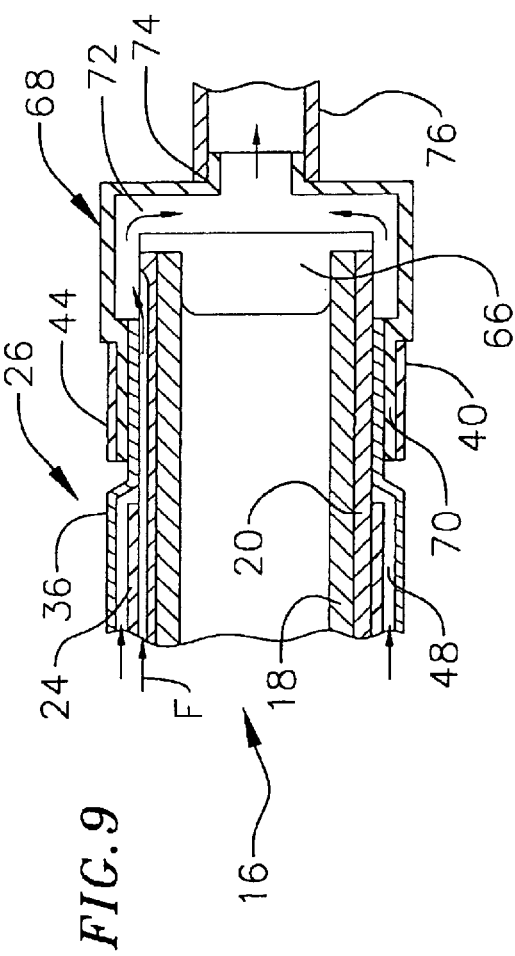

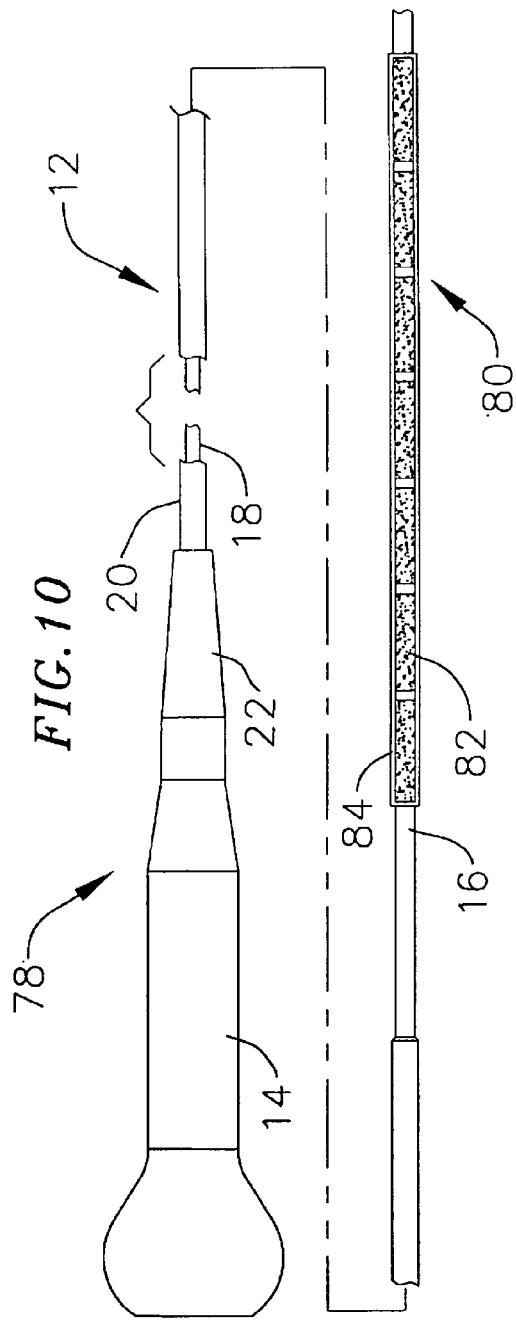
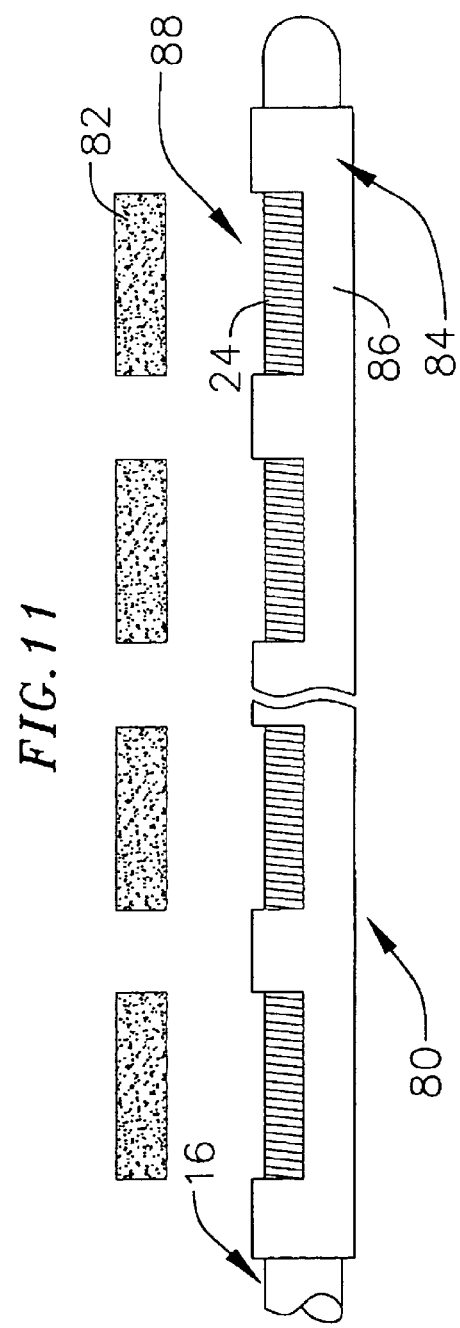

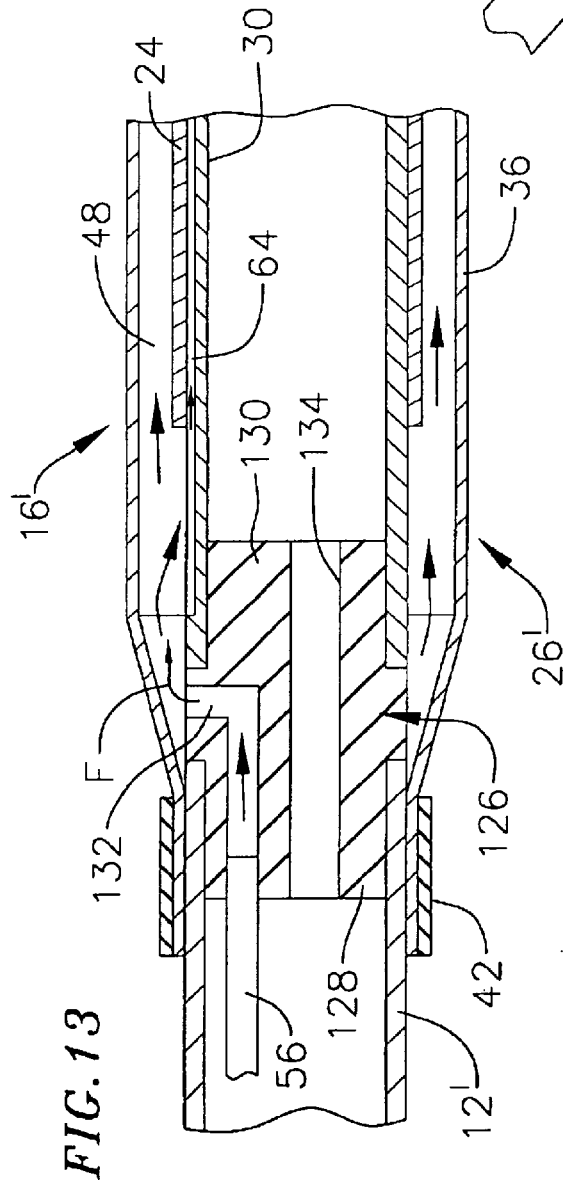
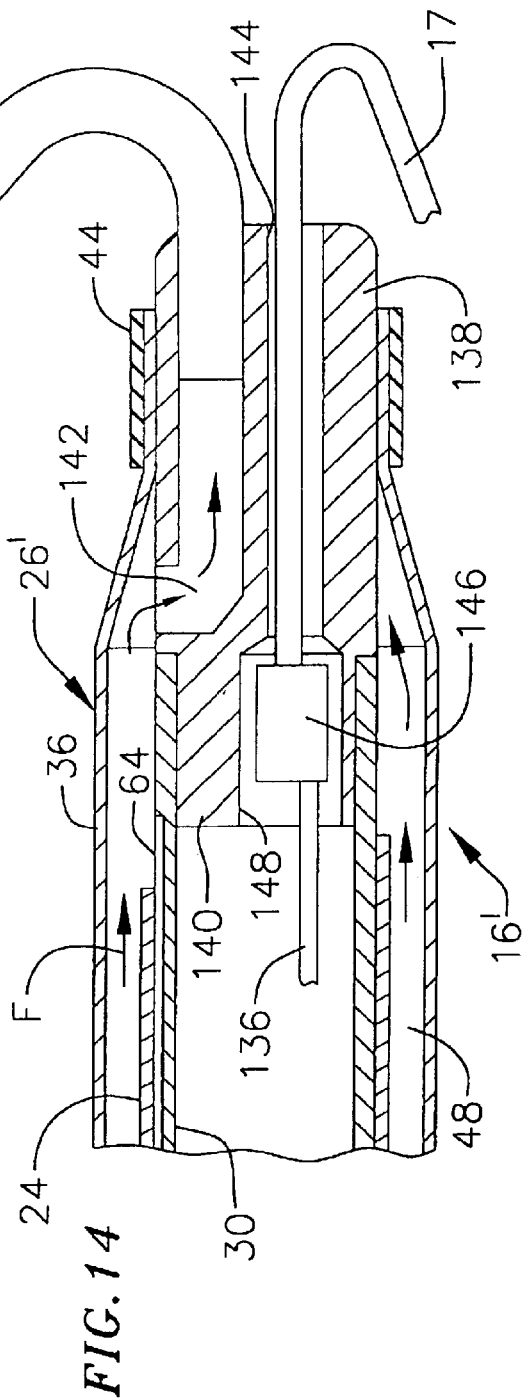

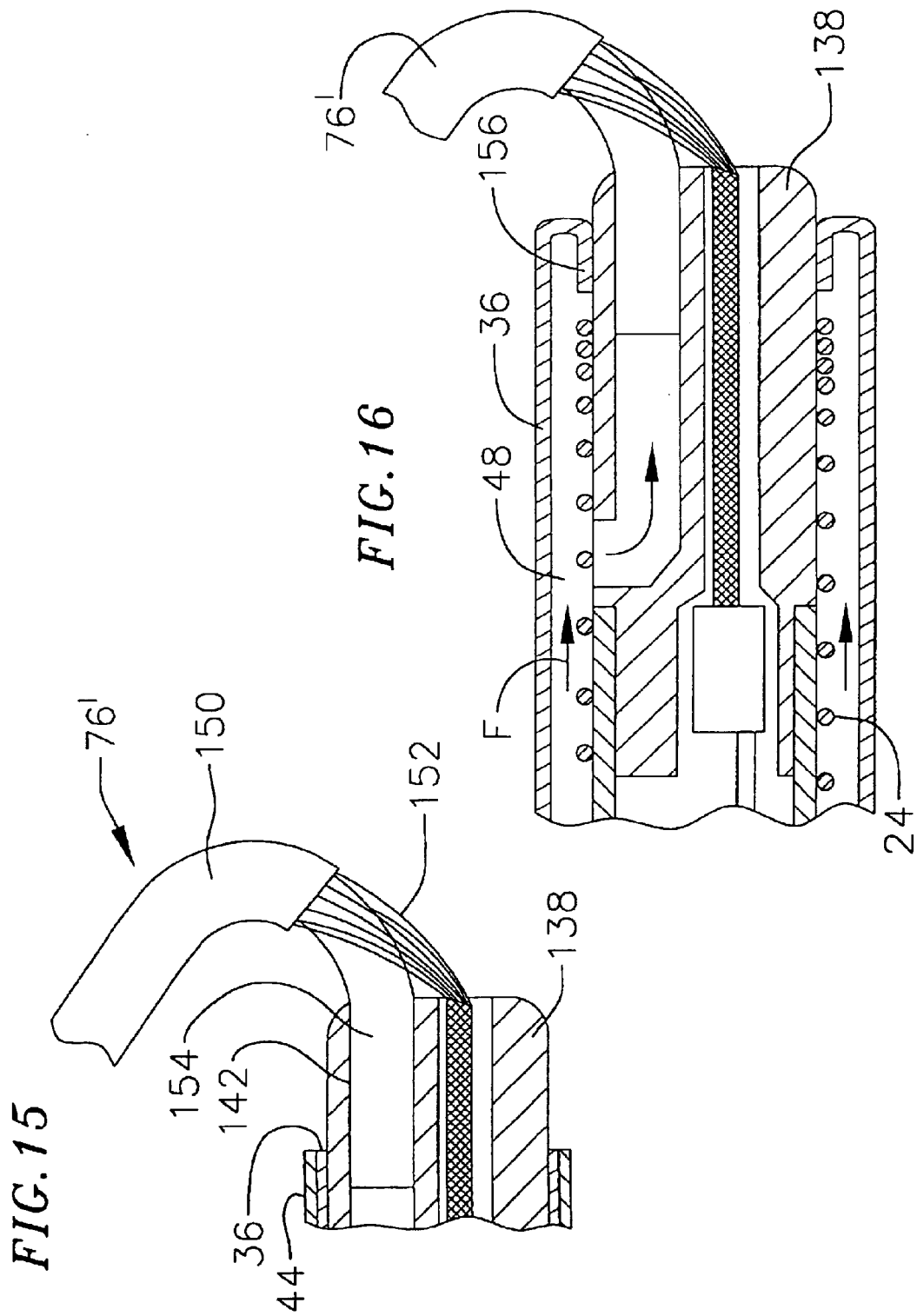

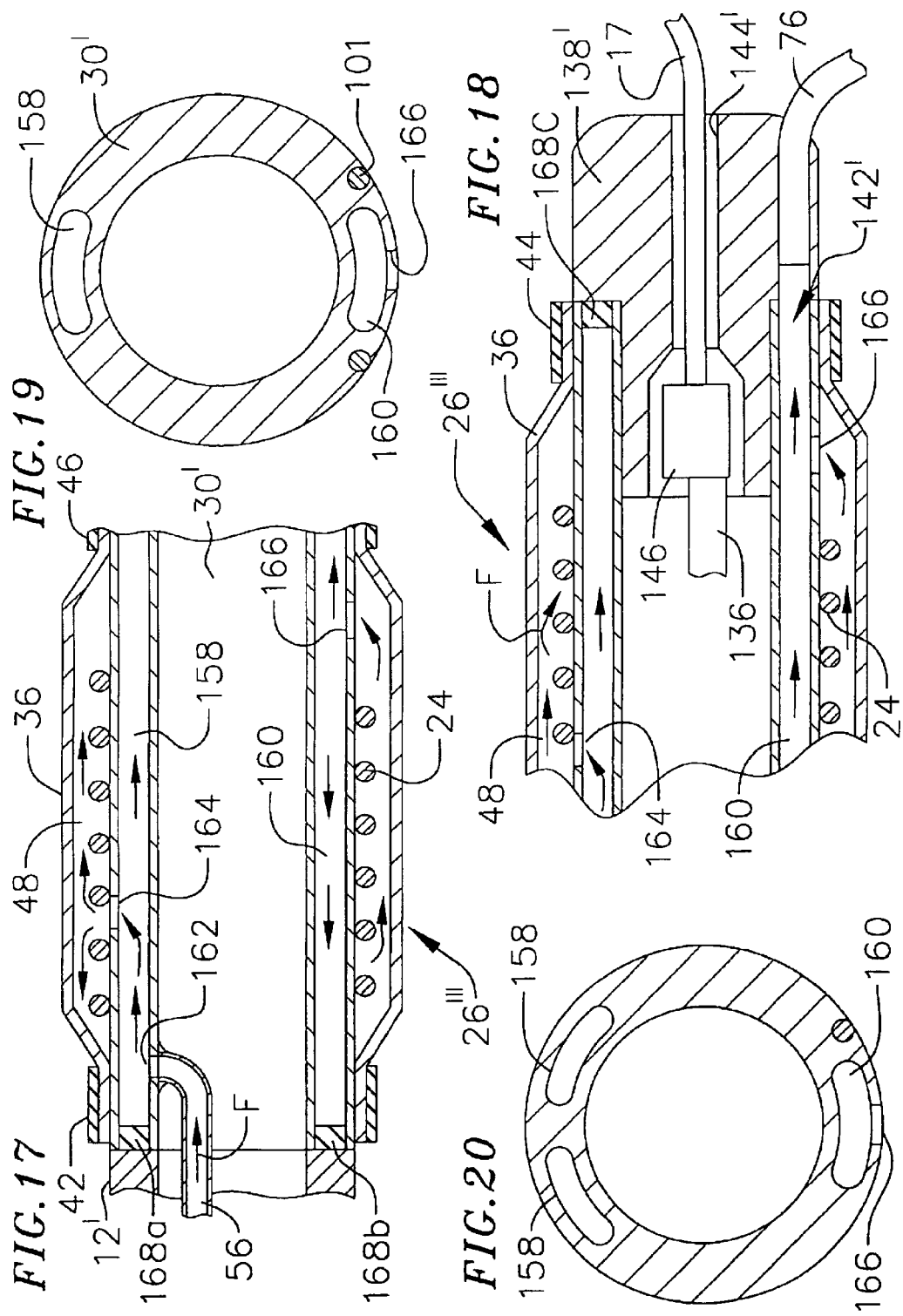

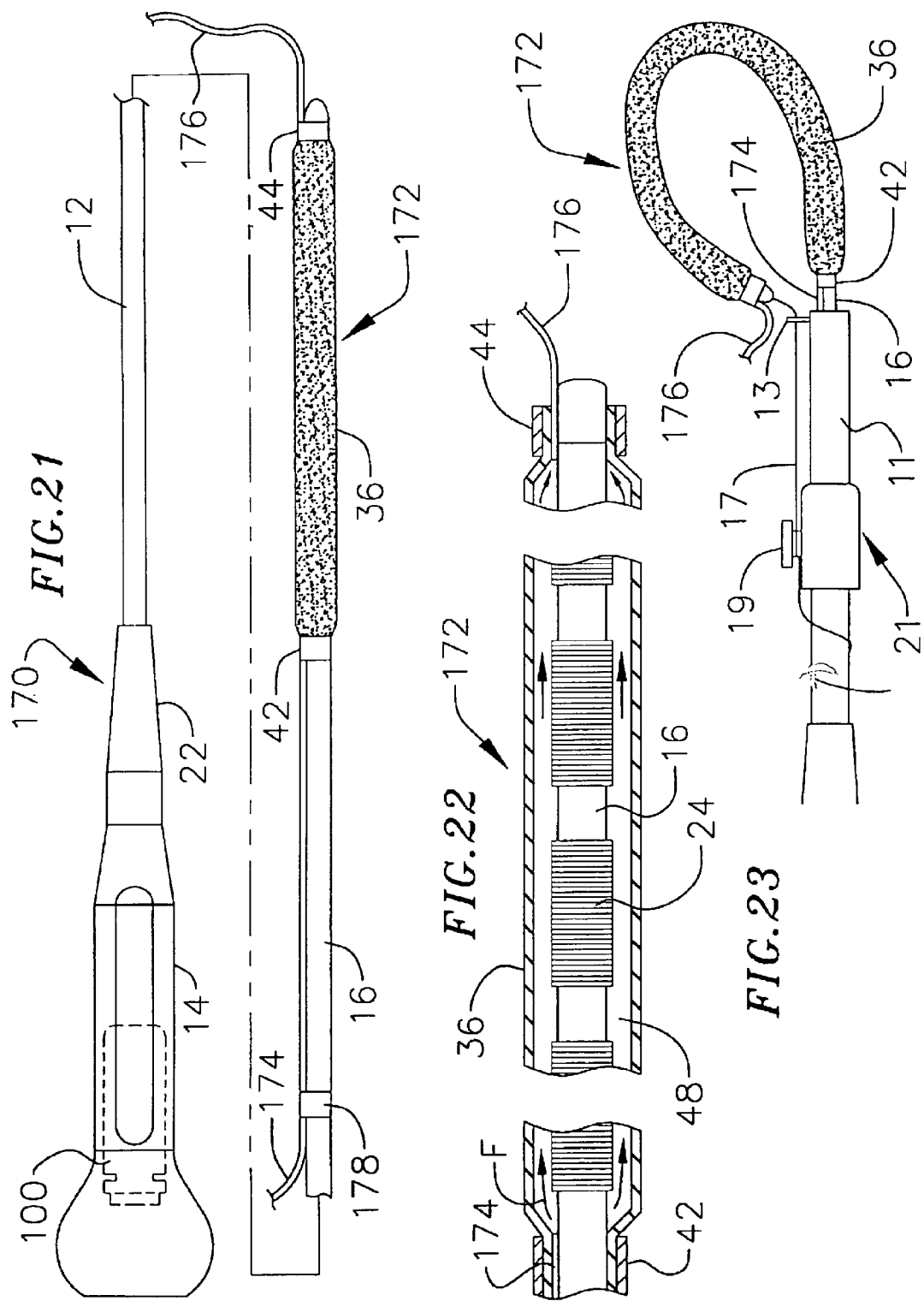

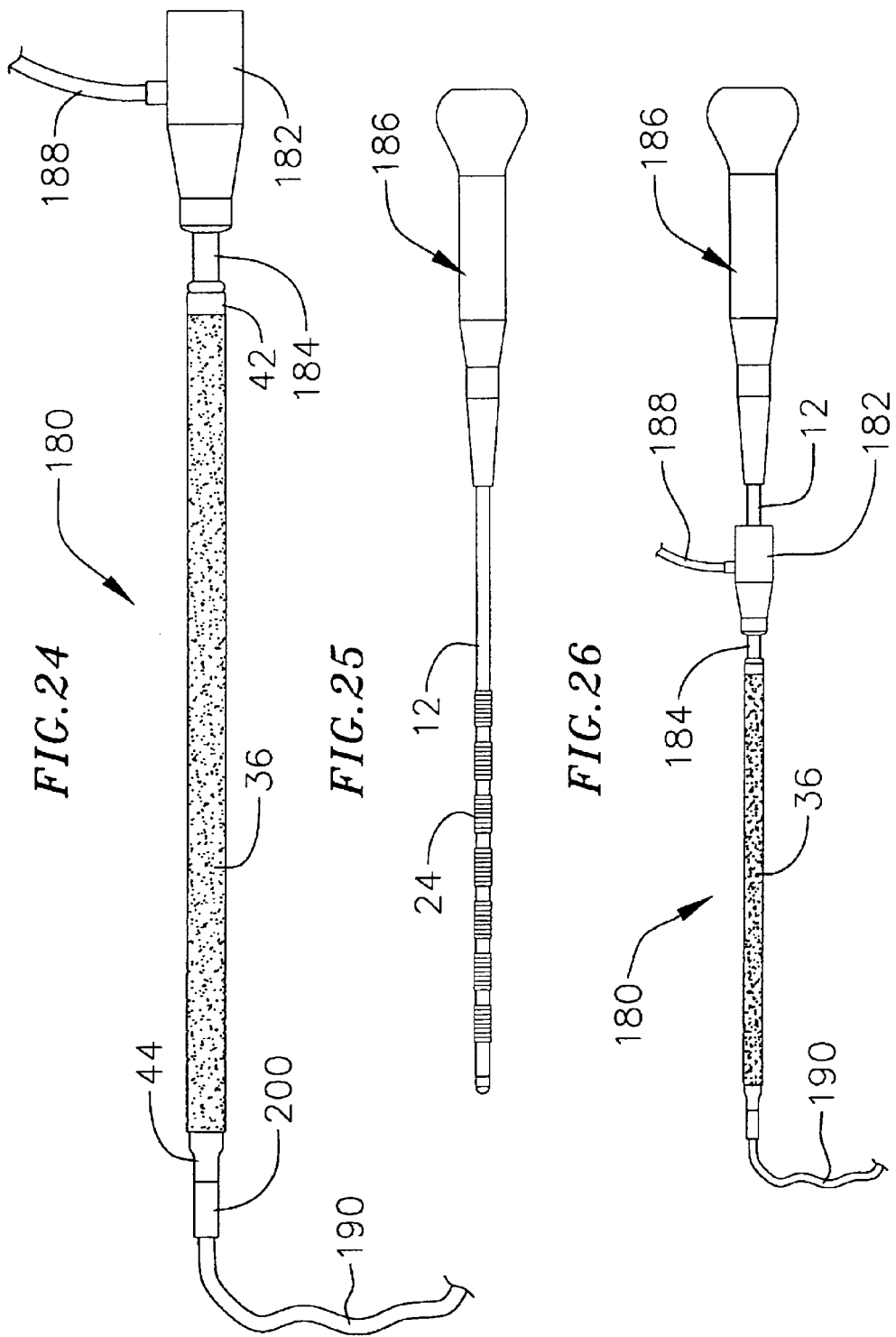

FLUID COOLED APPARATUS FOR SUPPORTING DIAGNOSTIC AND THERAPEUTIC ELEMENTS IN CONTACT WITH TISSUE

CROSS-REFERENCE TO RELATED APPLICATIONS

This application is a continuation-in-part of U.S. application Ser. No. 09/652,099, filed Aug. 30, 2000, now U.S. Pat. No. 6,579,288, which is incorporated herein by reference.

BACKGROUND OF THE INVENTIONS

1. Field of Inventions

The present inventions relate generally to structures for positioning diagnostic and therapeutic elements within the body and, more particularly, to devices which are particularly well suited for the treatment of cardiac conditions.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing catheters which can form lesions on the endocardium to effectively create a maze for electrical conduction in a predetermined path. Exemplary catheters are disclosed in commonly assigned U.S. Pat. No. 5,582,609. Typically, the lesions are formed by ablating tissue with an electrode carried by the catheter. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions (the lesions being 3 to 15 cm in length) typically include a relatively long and relatively flexible body portion that has one or more electrodes at or near its distal end. The portion of the catheter body portion that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter.

Catheter-based soft tissue coagulation has proven to be a significant advance in the medical arts generally and in the treatment of cardiac conditions in particular. Nevertheless, the inventors herein have determined that catheter-based procedures are not appropriate in every situation. It can be difficult to precisely position the distal portion of conventional catheters. It can also be difficult to achieve adequate tissue contact.

One particular lesion that has proven to be difficult to form with conventional catheters is the circumferential lesion that is used to isolate a pulmonary vein and cure ectopic atrial fibrillation. Lesions that isolate the pulmonary vein may be formed within the pulmonary vein itself or in the tissue surrounding the pulmonary vein. Lesions may be created such that a single circumferential lesion isolates a single pulmonary vein or such that a single circumferential lesion isolates more than one pulmonary vein. The circumferential lesions are formed by dragging a tip electrode around the pulmonary vein or by creating a group of interconnected curvilinear lesions one-by-one around the pulmonary vein. Such techniques have proven to be less than effective because they are slow and gaps of conductive tissue can remain after the procedure.

Endocardial lesions have also been formed as a secondary procedure during a primary open heart surgical procedure such as mitral valve replacement, aortic valve replacement, and coronary artery bypass grafting. A surgical soft tissue coagulation probe is used to form the endocardial lesions after the heart has been opened, either before or after the valve replacement. This technique has proven to be quite useful, especially for forming lesions that isolate pulmonary veins. It does, however, increase the amount of time the patient is on pulmonary bypass, which can be undesirable. The inventors herein have, therefore, determined that a need exists for surgical methods and apparatus that can be used to create lesions on bodily structures and, in the context of the treatment of atrial fibrillation, to create therapeutic lesions that do not require the patient to be on pulmonary bypass.

Another issue associated with lesion formation is tissue cooling. There are many instances where it is desirable to create lesions that are wider and deeper than those which can be created with conventional electrode structures. One method of increasing lesion size is to cool the tissue during the lesion formation process. Removal of heat from the tissue that is the closest to the coagulation electrodes shifts the hottest iso-thermal region deeper into the tissue, thereby enabling higher power to be delivered without causing char or excessive surface desiccation to occur. Higher power, in turn, results in a larger volume of tissue being heated to a temperature sufficient to coagulate tissue (above 50° C.) and, therefore, a wider and deeper lesion.

Although conventional tissue cooling methods have proven to be an advance in the art, the inventors herein have determined that conventional tissue cooling methods are susceptible to improvement and, in particular, that a need exists for tissue cooling apparatus that is well suited for use in the formation of elongate lesions.

SUMMARY OF THE INVENTIONS

Accordingly, the general object of the present inventions is to provide methods and apparatus that avoid, for practical purposes, the aforementioned problems. In particular, one object of the present inventions is to provide surgical methods and apparatus that can be used to create lesions in a more efficient manner than conventional apparatus. Another object of the present inventions is to provide surgical methods and apparatus that can be used to create lesions while the heart is beating. Still another object of the invention is to provide tissue cooling apparatus that may be used during the formation of elongate lesions which is superior to conventional cooling apparatus and suitable for epicardial and endocardial applications.

In order to accomplish some of these and other objectives, a device in accordance with a present invention includes a shaft, at least one energy transmission device and a tissue cooling apparatus. Such a device provides a number of advantages over the conventional lesion creation devices. The tissue cooling capability, for example, allows the present device to form wider and deeper lesions than the conventional surgical devices.

One particular implementation of the inventions is a surgical device with a relatively short shaft. Such surgical devices are especially useful in epicardial applications requiring continuous transmural lesions. In the context of the treatment of atrial fibrillation, for example, continuous transmural lesions may be created around one or more pulmonary veins while the heart is beating. Other epicardial lesions may also be created. The heart need not be opened and pulmonary bypass is not required. As such, the present devices advantageously allow curative lesions to be formed without the difficulties associated with catheter-based procedures or the time on pulmonary bypass required by conventional surgical procedures.

In some implementations, the tissue cooling apparatus includes an outer member positioned about the energy transmission device (or a plurality of energy transmission devices) such that a fluid transmission space is defined therebetween and a source that supplies conductive fluid to outer member inlet such that the conductive fluid flows from the inlet to the outlet while energy is being transmitted from the energy transmission device(s). During a lesion creation procedure, heat will be transferred from the tissue to the flowing conductive fluid thereby enabling the formation of wider and deeper lesions. In addition, because fresh fluid continues to be supplied to the inlet during the procedure, the amount of heat removed from the tissue is greater than it would be if the fluid remained stagnant within the space.

In accordance with another invention, a tissue cooling apparatus includes a base member that can be removably mounted on an electrophysiology apparatus and a fluid transfer assembly defining a size and shape sufficient to receive the distal portion of the electrophysiology apparatus shaft in such a manner that a fluid transmission space is defined between the electrophysiology apparatus shaft and the fluid transfer assembly. Such an apparatus may, for example, be used to provide an existing surgical probe with fluid cooling capabilities.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view showing a surgical probe in accordance with a preferred embodiment of a present invention.

FIG. 2 is a plan view of a portion of the distal section of the probe illustrated in FIG. 1 with the tissue cooling apparatus removed.

FIG. 3 is a section view taken along line 3—3 in FIG. 1.

FIG. 4 is a section view of an exemplary probe distal section.

FIG. 5 is a section view of another exemplary probe distal section.

FIGS. 6a and 6b are partial plan views together showing a surgical probe in accordance with a preferred embodiment of a present invention.

FIG. 8 is a section view of a portion of the distal section of the probe illustrated in FIG. 1.

FIG. 9 is a section view of another portion of the distal section of the probe illustrated in FIG. 1.

FIG. 10 is a plan view showing a surgical probe in accordance with a preferred embodiment of a present invention.

FIG. 11 is a partially exploded view of a distal portion of the probe illustrated in FIG. 10.

FIGS. 13 and 14 are partial section views of a tissue cooling apparatus in accordance with a preferred embodiment of a present invention.

FIG. 15 is a partial section view of an alternative drainage tube and pull wire arrangement.

FIG. 16 is a partial section view of an alternative distal end arrangement.

FIGS. 17 and 18 are partial section views of a tissue cooling apparatus in accordance with a preferred embodiment of a present invention.

FIG. 19 is a section view of a portion of the tissue cooling apparatus illustrated in FIGS. 17 and 18.

FIG. 20 is a section view showing an alternative version of the portion of the tissue cooling apparatus illustrated in FIG. 19.

FIG. 21 is a plan view showing a surgical probe in accordance with a preferred embodiment of a present invention.

FIG. 22 is a partial section view of the distal portion of the probe illustrated in FIG. 21.

FIG. 23 is a plan view of the distal portion of a surgical probe in accordance with a preferred embodiment of a present invention.

FIG. 24 is a plan view of a tissue cooling attachment in accordance with a preferred embodiment of a present invention.

FIG. 25 is a plan view of a surgical probe.

FIG. 26 is a plan view showing the surgical probe illustrated in FIG. 25 in combination with the tissue cooling attachment illustrated in FIG. 24.

DETAILED DESCRIPTION OF THE PREFERRED EMBODIMENTS

Figures 7A, 7B:
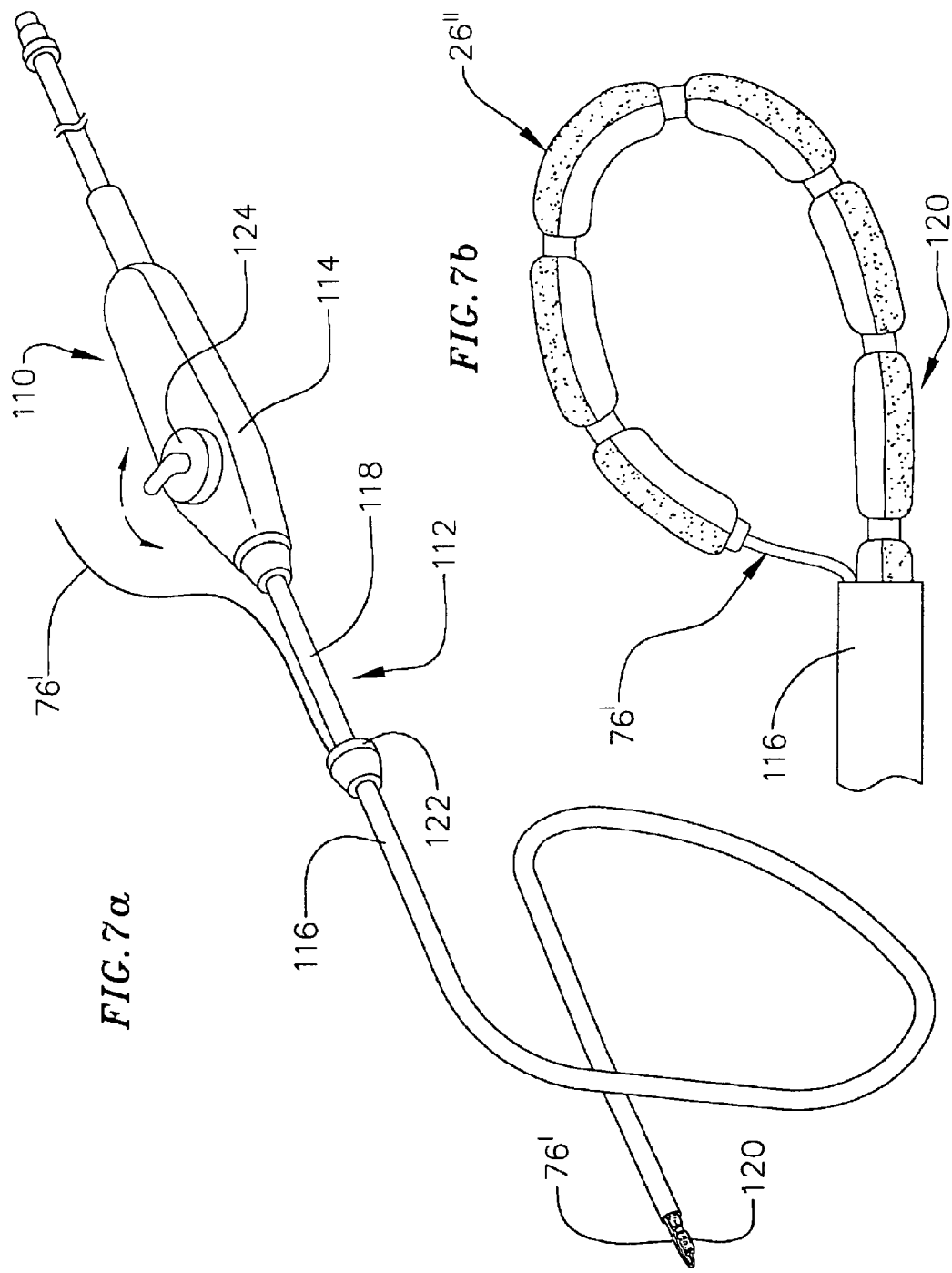
FIG. 7a is a perspective view of a catheter in accordance with a preferred embodiment of a present invention.
FIG. 7b is a side view of the distal region of the catheter illustrated in FIG. 7a in a loop orientation.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Probe Structures
II. Catheter Structures
III. Tissue Cooling Apparatus
IV. Electrodes, Temperature Sensing And Power Control
V. Exemplary Lesion Locations The section titles and overall organization of the present detailed description are for the purpose of convenience only and are not intended to limit the present inventions.

This specification discloses a number of structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Probe Structures

As shown by way of example in FIGS. 1–3, a surgical probe 10 in accordance with a preferred embodiment of a present invention includes a relatively short shaft 12, a handle 14 and a distal section 16. The shaft 12 consists of a hypotube 18, which is either rigid or relatively stiff, and an outer polymer tubing 20 over the hypotube. The handle 14 preferably consists of two molded handle halves and is provided with strain relief element 22. The shaft 12 in the illustrated embodiment may be from 4 inches to 18 inches in length and is preferably 6 to 8 inches. The distal section 16, which is preferably either malleable or somewhat flexible, may be from 1 inch to 10 inches in length and is preferably 2 to 3 inches. A plurality of electrodes 24, or other energy transmission devices, are provided on the distal section 16 of the exemplary embodiment. The electrodes 24 are discussed in greater detail in Section IV below. A tissue cooling apparatus 26 is positioned over the electrodes 24. The tissue cooling apparatus 26 is discussed in greater detail in Section III below.

As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:

W is the force applied normal to the longitudinal axis of the shaft,

L is the length of the shaft,

X is the distance between the fixed end of the shaft and the applied force,

E is the modulous of elasticity, and

I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$. Preferably, a relatively stiff 2 inch shaft will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

In those instances where a malleable shaft 12 is desired, the hypotube 18 may be the heat treated malleable hypotube covered by the outer tubing 20 illustrated in FIGS. 1 and 3. By selectively heat treating certain portions of the hypotube, one section of the hypotube can be made more malleable than the other. The outer tubing 20 may be formed from Pebax® material, polyurethane, or other suitable materials.

As noted above, the distal section 16 can be either somewhat flexible, in that it will conform to a surface against which it is pressed and then spring back to its original shape when removed from the surface, or malleable. A bending modulus of between 3 lb.-in.$^2$ and 50 lb.-in.$^2$ is preferred. As shown by way of example in FIG. 4, a somewhat flexible distal section 16 may include a spring member 28, which is preferably either a solid flat wire spring (as shown), a round wire, or a three leaf flat wire Nitinol spring, that is connected to the distal end of the hypotube 18. Other spring members, formed from materials such as 17-7 or carpenter's steel, may also be used. The spring member 28 is enclosed in a flexible body 30, preferably formed from Pebax® material, polyurethane, or other suitable materials. The spring member 28 may also be pre-stressed so that the distal tip is pre-bent into a desired shape. An insulating sleeve 32 is placed over the spring member 28 in the exemplary embodiment. The insulating sleeve protects the conductor wires 98 and signal wires 102, which are discussed in Section IV below. It should be noted here that the conductor wires 98 and signal wires 102 have been removed from the majority of the figures for purposes of clarity.

In those instances where a malleable distal section 16 is desired, the spring member 28 may be replaced by a mandrel 34 made of suitably malleable material such as annealed stainless steel or beryllium copper, as illustrated for example in FIG. 5. The malleable mandrel may be fixed directly within the distal end of the shaft's hypotube 18 and secured by, for example, soldering, spot welding or adhesives. Alternatively, the distal section 16 may be formed by a hypotube that is simply a continuation of the shaft hypotube 18 covered by a continuation of the outer tubing 20 (as shown in FIGS. 8 and 9). However, the distal end hypotube can also be a separate element connected to the shaft hypotube 18, if it is desired that the distal end hypotube have different stiffness (or bending) properties than the shaft hypotube.

Another alternative arrangement is to have a distal section 16 that has a malleable proximal portion and a flexible distal portion. For example, the distal section 16 may include a shorter malleable mandrel 38 and a shorter spring member 28 that are secured to one another with a crimp tube. Such an arrangement is described in greater detail in U.S. application Ser. No. 09/536,095, which is entitled "Loop Structure For Positioning Diagnostic Or Therapeutic Element On The Epicardium Or Other Organ Surface" and incorporated herein by reference.

Surgical probes in accordance with other embodiments of the present inventions include distal sections that can be manipulated into a loop. Such probes include many structural elements similar to those in the exemplary devices illustrated in FIGS. 1–5 and such elements are represented by the same reference numerals. As illustrated for example in FIGS. 6a and 6b, a surgical probe 10' includes a relatively short shaft 12', a handle 14 and a distal section 16'. The shaft 12', which is more flexible than the shaft 12 and less flexible than the distal section 16', is typically formed from a biocompatible thermoplastic material that is thermally and electrically insulating, such as a braided Pebax® material. The shaft 12' and distal section 16' may be bonded together with an overlapping thermal bond or adhesively bonded together end to end over a sleeve in what is referred to as a "butt bond." Preferably, however, the shaft 12' and distal section 16' will be secured to one another in the manner described below with reference to FIGS. 13 and 14.

Exemplary probe 10' is provided with a relatively short outer member 11 that has a pull wire guide 13 and a flared inner surface (not shown) or soft material at its distal end and a locking device 15, such as a Toughy Borst fitting, at its proximal end to fix the position of the shaft 12'. A pull wire 17 may be threaded through the pull wire guide 13 to form a loop and then secured to the post 19 on an anchoring device 21. The loop may be adjusted by moving the shaft 12' and outer member 11 relative to one another or by adjusting the pull wire 17. The outer member 11 is preferably formed from relatively high durometer materials (72D and above), such as braided or unbraided Pebax® or Nylon material, that is stiffer than the distal section 16' as well as thermally and electrically insulating. The outer member 11 should also be slightly shorter (i.e. 1 to 2 inches shorter) than the shaft 12'.

Like the exemplary probe illustrated in FIGS. 1–5, the distal section 16' of the exemplary probe 10' supports a plurality of electrodes 24 and a tissue cooling apparatus 26'. The electrodes 24 are discussed in greater detail in Section IV below and the tissue cooling apparatus 26' is discussed in greater detail in Section III below.

The exemplary probe 10' may also be provided without the outer member 11. Here, the pull wire 17 could be used to pull the distal section around anatomical structures as needed. Such a probe would preferably have a distal section 16 that included the malleable proximal portion and flexible distal portion described above. Additional details concerning these and other surgical probes that may be manipulated into loops may be found in aforementioned U.S. application Ser. No. 09/536,095.

II. Catheter Structures

The present inventions also have application in catheters, such as the catheter 110 illustrated in FIGS. 7a and 7b, which are percutaneously directed to a target tissue region. The exemplary catheter 110 includes a catheter tube 112 that is secured to a handle 114 and an outer tube (or sheath) 116 through which the catheter tube is advanced. The catheter tube 112 is formed from a relatively long proximal section 118 and a shorter distal section 120 that supports a plurality of electrodes 24 (not visible in FIGS. 7a and 7b). A tissue cooling apparatus 26" is positioned over the electrodes 24. The electrodes 24 are discussed in greater detail in Section IV below and the tissue cooling apparatus 26" is discussed in greater detail in Section III below.

The proximal section 118 may be formed from a biocompatible thermoplastic material that is thermally and electrically insulating, such as a braided Pebax® material, while the distal section 120 may be formed from a softer, more flexible biocompatible thermoplastic material that is also thermally and electrically insulating, such as Pebax® material, polyethylene, or polyurethane. The proximal and distal sections are preferably either bonded together with an overlapping thermal bond, adhesively bonded together end to end over a sleeve in what is referred to as a "butt bond," or secured to one another in the manner illustrated in FIG. 13. The outer tube 116, which is fitted with a handle 122, should have a greater inherent stiffness than the electrode supporting distal section 120. Preferably, the material is relatively thin (e.g., with a wall thickness of about 0.013 inch) so as not to significantly increase the overall diameter of the catheter 110 (about 9 French) and lubricious to reduce friction during relative movement of the catheter tube 112. A suitable material is polyvinylidene fluoride (PTFE).

Exemplary catheter 110 also includes a drainage tube 76' (discussed in detail in Section III below with reference to FIG. 15) that, in addition to its drainage function, functions in the same manner as a pull wire in a conventional loop catheter. More specifically, a loop such as that illustrated in FIG. 7b may be formed by advancing the catheter tube 112 in the distal direction from the position illustrated in FIG. 7a while holding the outer tube 116 and drainage tube 76' in place. Once the loop has been formed, the physician can pull on the drainage tube 76' to decrease its exposed length beyond the distal end of the outer tube 116. Further adjustments to the loop may be made by advancing or retracting the catheter tube 112 within the sheath outer tube.

A catheter steering mechanism may also be provided so that additional tissue contact forces can be generated. In a preferred embodiment, a bendable steering spring (not shown) is mounted within the distal section 120. One or more steering wires are bonded to the steering spring and extend back to a control knob 124 on the handle 114. The control knob 124 pulls on the steering wires to apply bending forces to the steering spring. Additional details concerning steering and other aspects of loop catheter structures may be found in U.S. Pat. No. 6,048,329, which is entitled "Catheter Distal Assembly With Pull Wires" and incorporated herein by reference.

III. Tissue Cooling Apparatus

Figure 12:
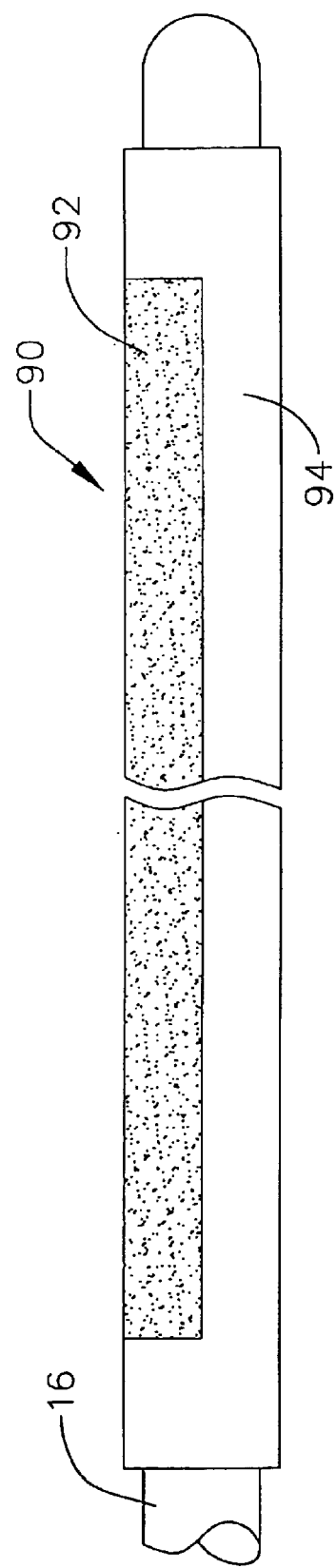
FIG. 12 is a plan view of a tissue cooling apparatus in accordance with a preferred embodiment of a present invention.

The tissue cooling apparatus disclosed herein employ conductive fluid to cool tissue during coagulation procedures. More specifically, and ,as described in greater detail below, heat from the tissue being coagulated is transferred to ionic fluid to cool the tissue while energy is transferred from an electrode or other energy transmission device to the tissue through the fluid by way of ionic transport. The conductive fluid may be pumped through the tissue cooling apparatus and preferably continuously (FIGS. 1, 2, 6a–9 and 13–29) or the tissue cooling apparatus may be saturated with the fluid prior to use (FIGS. 10–12). In either case, cooling tissue during a coagulation procedure facilitates the formation of lesions that are wider and deeper than those that could be realized with an otherwise identical device which lacks the present tissue cooling apparatus.

Turning first to the preferred embodiment illustrated in FIGS. 1–5, 8 and 9, the tissue cooling apparatus 26 includes a microporous outer casing 36 through which ionic fluid is transferred from one end of the cooling apparatus to the other. The outer casing 36 is secured to the probe distal section 16 over the electrodes 24. More specifically, the proximal and distal ends 38 and 40 of the outer casing 36 are secured to the distal section 16 with anchoring devices 42 and 44. The outer casing 36 is also secured to the distal section 16 between each of the electrodes 24 by intermediate anchoring devices 46. Suitable anchoring device include lengths of heat shrink tubing, Nitinol tubing or other mechanical devices that form an interference fit between the casing 36 and the distal section 16. Adhesive bonding is another method of securing the outer casing 36 to the distal section 16. Regardless of the method used to secure the outer casing 36 to the distal section 16, a fluid transmission space 48 (FIGS. 8 and 9), which is typically about 0.005 to 0.020 inch, but can be as large as 0.1 inch, should remain between the inner surface of the outer casing and the outer surface of the electrodes 24.

Referring more specifically to FIGS. 1, 2 and 8 and 9, the ionic fluid (represented by arrows F) flows through the illustrated embodiment as follows. First, the ionic fluid is supplied under pressure from a fluid source 50 to a fluid inlet port 52 in the handle 14 by way of an outer supply line 54. An inner supply line 56 extends from the fluid inlet port 52 to the distal section 16. The distal end 58 of the inner supply line 56 terminates at an aperture 60 that extends through hypotube 18 and outer tubing 20. Adhesive 62, or other suitable instrumentalities, may be used to secure the distal end 58 of the inner supply line 56 to the inner surface of the hypotube 18.

The aperture 60 terminates within a channel 64 that is formed on the outer surface of the outer tubing 20. The channel 64 allows the ionic fluid to flow beneath the proximal end 38 of the outer casing 36, beneath the proximal anchoring device 42 and into the fluid transmission space 48. The channel 64 preferably extends from a region proximal to the proximal-most electrode 24 to a region distal of the distal most electrode. [Note FIG. 2.] Once within the proximal-most region of the fluid transmission space 48, the ionic fluid will surround the proximal-most electrode 24 and flow between the outer surface of the electrode and the inner surface of the outer casing 36. [Note FIG. 8.] The ionic fluid will also flow under the electrode 24 via the channel 64. The ionic fluid flowing over the outer surface of the electrode 24 will re-enter the channel 64 when it reaches the proximal-most anchoring device 46, dip under the anchoring device, exit the channel (some fluid will, of course, remain in the channel), and enter the next fluid transmission space. This pattern will continue until the ionic fluid reaches the distal end of the distal section 16.

Additional channels 64 may also be provided to facilitate fluid flow. For example, one or more additional channels that extend from the proximal-most fluid transmission space 48 to the region distal of the distal-most electrode 24 may be formed in the outer tubing 20. Alternatively, the additional channels may be identical to channel 64 in that they are connected to the inner supply line 56 by way of branches in the supply line and apertures that extend through the hypotube 18 and outer tubing 20. The width and depth of the channels 64 will depend upon the desired flow rate and the total number of channels. In a preferred implementation that includes two channels 64, the channels are 0.02 inch wide and 0.08 inch deep.

As illustrated for example in FIG. 9, the distal end of the distal section 16 preferably includes a resilient stopper 66, which prevents the ionic fluid from entering the hypotube 18, and an end cap 68. The resilient stopper 66 is secured to the distal opening in the hypotube 18 with adhesive. The exemplary end cap 68 includes a flange 70 that is positioned between the outer casing distal end 40 and the anchor 44 during assembly. The end cap 68 also includes an interior region 72 and an outlet port 74. Ionic fluid exiting the channel (or channels) 64 flows into the interior region 72 and then out through the outlet port 74 into a drainage tube 76. The drainage tube 76 directs the now heated ionic fluid into a receptacle outside the patient. Removal of the heated ionic fluid is important because it will be hot enough (typically about 60° C. when it reaches the distal end of the probe) to burn the patient if allowed to drip into the thorax.

The electrically conductive ionic fluid preferably possesses a low resistivity to decrease ohmic loses, and thus ohmic heating effects, within the microporous outer casing 36. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution.

With respect to temperature and flow rate, a suitable inlet temperature for epicardial applications (the temperature will, of course, rise as heat is transferred to the fluid) is about 0 to 25° C. with a constant flow rate of about 2 to 20 ml/min. The flow rate required for endocardial applications where blood is present would be about three-fold higher (i.e. 6 to 60 ml/min.). Should applications so require, a flow rate of up to 100 ml/min. may be employed. In a closed system where the fluid is stored in a flexible bag, such as the Viaflex® bag manufactured by Baxter Corporation, and heated fluid is returned to the bag, it has been found that a volume of fluid between about 200 and 500 ml within the bag will remain at room temperature (about 22° C.) when the flow rate is between about 2 ml/min. and 20 ml/min. Alternatively, in an open system, the flexible bag should include enough fluid to complete the procedure. 160 ml would, for example, be required for a 20 minute procedure where the flow rate was 8 ml/min.

The fluid pressure within the microporous outer casing 36 should be about 30 mm Hg in order to provide a structure that will resiliently conform to the tissue surface in response to a relatively small force normal to the tissue. Pressures above about 100 mm Hg will cause the outer casing 36 to become too stiff to properly conform to the tissue surface. For that reason, the flow resistance to and from the outer casing 36 should be relatively low.

The pores in the microporous outer casing 36 allow the transport of ions contained in the fluid through the casing and into contact with tissue. Thus, when the electrodes 24 transmit RF energy into the ionic fluid, the ionic fluid establishes an electrically conductive path through the outer casing 36 to the tissue being coagulated. Regenerated cellulose membrane materials, typically used for blood oxygenation, dialysis, or ultrafiltration, are a suitable microporous material for the outer casing 36. The thickness of the material should be about 0.002 to 0.005 inch. Although regenerated cellulose is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within the outer casing 36.

Hydro-Fluoro™ material, which is disclosed in U.S. application Ser. No. 09/573,071, filed May 16, 2000 (incorporated herein by reference), is another material that may be used. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. Microporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur. Considerations of overall porosity (discussed below) and perfusion rates must be taken more into account as pore size increases.

The electrical resistivity of the outer casing 36 will have a significant influence on lesion geometry and controllability. Low-resistivity (below about 500 ohm-cm) requires more RF power and results in deeper lesions, while high-resistivity (at or above about 500 ohm-cm) generates more uniforn heating and improves controllability. Because of the additional heat generated by the increased body resistivity, less RF power is required to reach similar tissue temperatures after the same interval of time. Consequently, lesions generated with high-resistivity structures usually have smaller depth. The electrical resistivity of the outer casing can be controlled by specifying the pore size of the material, the porosity of the material, and the water adsorption characteristics (hydrophilic versus hydrophobic) of the material. A detailed discussion of these characteristics is found in U.S. Pat. No. 5,961,513, which is entitled "Tissue heating and Ablation Systems and Methods Using Porous Electrode Structures" and is incorporated herein by reference. A suitable electrical resistivity for epicardial and endocardial lesion formation is about 1 to 3000 ohm-cm measured wet.

Generally speaking, low or essentially no liquid perfusion through the microporous outer casing 36 is preferred. When undisturbed by attendant liquid perfusion, ionic transport creates a continuous virtual electrode at the electrode body-tissue interface. The virtual electrode efficiently transfers RF energy without need for an electrically conductive metal surface.

In preferred implementations, the pores will only be located on the side of the probe that is intended to contact tissue. [Note FIG. 7b.] Such an arrangement directs coagulating energy from the electrodes directly toward and into the intended tissue and prevents collateral damage by blocking transmission of energy into adjacent, non-target tissue. In the context of epicardial lesion creation, such non-target tissue may include the phrenic nerve and lung tissue.

Pore diameters smaller than about 0.1 $\mu$m retain macromolecules, but allow ionic transfer through the pores in response to the applied RF field. With smaller pore diameters, pressure driven liquid perfusion through the pores is less likely to accompany the ionic transport, unless relatively high pressure conditions develop within the outer casing 36. Larger pore diameters (up to 8 $\mu$m) can also be used to permit ionic current flow across the membrane in response to the applied RF field. With larger pore diameters, pressure driven fluid transport across the membrane is much higher and macromolecules (such as protein) and even small blood cells (such as platelets) could cross the membrane and contaminate the inside of the probe. Red blood cells would normally not cross the membrane barrier, even if fluid perfusion across the membrane stops. On balance, a pore diameter of 1 to 5 $\mu$m is suitable for epicardial and endocardial lesion formation. Where a larger pore diameter is employed, thereby resulting in significant fluid transfer through the porous region, a saline solution having a sodium chloride concentration of about 0.9% weight by volume would be preferred.

With respect to porosity, which represents the volumetric percentage of the outer casing 36 that is composed of pores and not occupied by the casing material, the magnitude of the porosity affects electrical resistance. Low-porosity materials have high electrical resistivity, whereas high-porosity materials have low electrical resistivity. The porosity of the outer casing 36 should be at least 1% for epicardial and endocardial applications employing a 1 to 5 $\mu$m pore diameter.

Turning to water absorption characteristics, hydrophilic materials are generally preferable because they possess a greater capacity to provide ionic transfer of RF energy without significant liquid flow through the material.

Certain other considerations are applicable to those embodiments which are catheter-based or otherwise endocardial in nature and, therefore, operate within the blood pool. Most notably, there should be essentially no liquid perfusion. This limits salt or water overloading caused by transport of the hypertonic solution into the blood pool. This is especially true when the hypertonic solution includes potassium chloride. Additionally, the ionic transport rate should below about 10 mEq/min when the hypertonic solution includes potassium chloride.

A probe 78 with another exemplary tissue cooling apparatus is illustrated in FIGS. 10 and 11. The tissue cooling apparatus 80 consists of a plurality of wettable fluid retention elements 82 that are simply saturated with ionic fluid such as saline prior to use, as opposed to having the fluid continuously pumped through the apparatus in the manner described above with reference to FIGS. 1–5, 8 and 9. But for the structures used to transfer fluid to the distal section of the probe, the underlying probe structures are the same as those described above with reference to FIGS. 1–5, 8 and 9. Similar reference numerals are used to represent similar elements.

The fluid retention elements 82 are mounted over respective electrodes 24 with a mounting body 84. The mounting body 84, which includes a side wall 86 defining an interior bore and a plurality of openings 88, is preferably formed from material that is electrically and thermally insulating so that coagulation energy from the electrodes 24 will only be transmitted through the openings. In addition to cooling, such an arrangement will mask the portions of the electrodes 24 that are not intended to contact tissue or blood. This arrangement also directs coagulating energy directly toward and into the intended tissue and prevents collateral damage by blocking transmission of energy into adjacent, non-target tissue.

The exemplary mounting body 84 is preferably formed from biocompatible plastics that are commonly used in catheters, such as Pebax® material and polyurethane, and is secured to the surgical device with an adhesive. Alternatively, the mounting body 84 may be formed from an elastic material that will hold the tissue cooling apparatus 80 on the distal section 16, yet also allow the surgeon to rotate the mounting body to focus the coagulation energy, or remove the tissue cooling apparatus altogether, as desired. A suitable elastic material is silicone rubber having a thickness that ranges from about 0.05 mm to about 1 mm, depending on the desired level of insulation.

Suitable materials for the fluid retention elements 82 include biocompatible fabrics commonly used for vascular patches (such as woven Dacron®), open cell foam materials, hydrogels, macroporous balloon materials (with very slow fluid delivery to the surface), and hydrophilic microporous materials. The effective electrical resistivity of the fluid retention elements 82 when wetted with 0.9% saline (normal saline) should range from about 1$\Omega$-cm to about 2000$\Omega$-cm. A preferred resistivity for epicardial and endocardial procedures is about 1000$\Omega$-cm.

Because it is important that the physician be able to identify the electrodes 24 or other operative elements that are in contact with tissue, the exemplary mounting body 84 should either be transparent or be provided with indicia (not shown) that allows the physician to distinguish between the electrodes. Such indicia, which may be printed directly onto the mounting body 84 with biocompatible ink, includes color coding, alpha-numeric indicia and shading.

The exemplary embodiment illustrated in FIGS. 10 and 11 includes a separate fluid retention element for each electrode 24. Alternatively, as illustrated in FIG. 12, exemplary tissue cooling apparatus 90 includes a single wettable fluid retention element 92 that covers all of the electrodes 24 and a mounting body 94 with a single opening.

The exemplary tissue cooling apparatus 26', which may be used in conjunction with a probe that includes a distal section that can be manipulated into a loop (such as that illustrated in FIGS. 6a and 6b), is illustrated in detail in FIGS. 13 and 14. Many aspects of the tissue cooling apparatus illustrated in FIGS. 13 and 14 are the same as those described above with reference to FIGS. 8 and 9. Similar reference numerals are used to represent similar elements.

Referring first to FIG. 13, tissue cooling apparatus 26' includes a connector 126 that connects the shaft 12' to the distal section 16'. The exemplary connector 126 has a proximal member 128 that is inserted into the shaft 12' and a distal member 130 that is inserted into the distal section flexible body 30. These components may be secured to one another with adhesive or other suitable instrumentalities. Connector 126 also includes a fluid lumen 132 and a central lumen 134. The inner supply line 56 is connected to one end of the fluid lumen 132. Ionic fluid from the inner supply line 56 exits the other end of the fluid lumen 132 into the fluid transmission space 48. The ionic fluid will then travel distally from one fluid transmission space 48 to another in the manner described above. The central lumen 134 provides a passage way for the conductor wires 98 and signal wires 102 (discussed in Section IV below with reference to FIGS. 3–5). A core wire 136 (FIG. 14), which may be provided in probes such as that illustrated in FIGS. 6a and 6b, will also pass through the central lumen 134.

The ionic fluid exits the tissue cooling apparatus 26' by way of the exemplary tip 138 illustrated in FIG. 14. The tip 138 includes a proximal member 140 that is inserted into (and secured to) the distal end of the flexible body 30. An outlet lumen 142 receives ionic fluid from the distal-most fluid transmission space 48 and transfers the fluid to the drainage tube 76. The tip 138 also includes a pull wire lumen 144 for the pull wire 17. The pull wire 17 is secured to the core wire 136 with a crimp tube 146 located within an expanded region 148 of the pull wire lumen 144.

The exemplary tissue cooling apparatus 26", which may be used in conjunction with catheter 110 illustrated in FIGS. 7a and 7b, is essentially identical to the tissue cooling apparatus 26' illustrated in FIGS. 13 and 14. Here, however, the pull wire and drainage tube are combined into an essentially unitary structure. As illustrated for example in FIG. 15, drainage tube 76' is formed from a braid tube with the outer portion 150 removed in the vicinity of its distal end to expose the braids 152. Alternatively, a braid tube with the braids on the exterior may be used. In either case, the braids 152 are separated from the remainder of the tube and connected to the core wire 136 with the crimp tube 146 in the manner illustrated in FIG. 14. The inner portion 154 of the braid tube is positioned within the tip outlet lumen 142. So configured, the drainage tube 76' may be used to perform the pull wire function in a loop catheter (or probe) in addition to the drainage function.

The distal end of the microporous outer casing 36 may be secured to the tip 138 in the manner illustrated for example in FIG. 16 for those applications which require the distal most tissue heating portion to be closer to the distal end of the catheter (or probe). Here, instead of being bent distally and secured with an anchor in the manner illustrated in FIG. 14, the outer casing distal end 156 is bent inwardly and secured to the tip 138 with adhesive. This configuration results in the distal-most transmission space 48 being closer to the distal end of the catheter and, therefore, extends the tissue heating portion of the catheter closer to the distal end than it is in the exemplary embodiment illustrated in FIG. 14.

The ionic fluid may also be fed from a common supply lumen to each of the individual transmission spaces 48, as opposed to being fed from one transmission space to another in the manner illustrated in FIGS. 1–16. The exemplary tissue cooling apparatus 26''' illustrated in FIGS. 17–19, which may be used in conjunction with any of the probes and catheters disclosed herein (with modifications as necessary), includes manifold-like ionic fluid lumens 158 and 160. The inner supply line 56 is connected to ionic fluid lumen inlet 162 and the ionic fluid lumen 158 is individually connected to each of the fluid transmission spaces 48 by transmission space respective inlets 164. Once a steady state has been achieved, the fluid lumen 158 will be filled with fluid under pressure and will be feeding each of the fluid transmission spaces 48 simultaneously. The ionic fluid exits each of the fluid transmission spaces 48 by way of respective outlets 166 which are connected to ionic fluid lumen 160. The distal tip 138' includes an outlet lumen 142' through which fluid from the ionic fluid lumen 160 passes on its way to the drainage tube 76. A pull wire lumen 144' for the pull wire 17 is also provided.

In the preferred embodiment, the flexible body 30' is a multi-lumen extrusion formed from Pebax® material, polyurethane, or other suitable materials. The proximal ends of the ionic fluid lumens 158 and 160 closed with plugs 168a and 168b, while the distal end of the lumen 158 is closed with a plug 168c.

The exemplary inlets and outlets 164 and 166 may be equally sized from one end of the tissue cooling apparatus 26''' to the other. The size of the inlets and outlets 164 and 166 may, however, progressively increase from the proximal end to the distal end in order to insure equal flow rates from one fluid transmission space 48 the next. Alternatively, the number of inlets and outlets 164 and 166 can increase with, for example, the proximal three fluid transmission spaces 48 each having a single inlet and outlet and the distial four fluid transmission spaces each having two inlets and outlets.

Dual ionic fluid lumens 158 may also be provided. [FIG. 20.] Dual inlet side lumens provide greater flow, as compared to a single lumen, and can be configured such that one of inlet side lumens feeds the distal three inlets and the other lumen feeds the other inlets.

Turning to FIGS. 21 and 22, a probe 170 in accordance with another exemplary embodiment includes a tissue cooling apparatus 172 that is similar to the tissue cooling apparatus 26 described above with reference to FIG. 1. For example, the tissue cooling apparatus 172 includes a microporous outer casing 36 mounted on the probe distal section 16 over the electrodes 24. The proximal and distal ends of the outer casing 36 are also secured with anchoring devices 42 and 44 that are preferably formed from heat shrink tubing. The tissue cooling apparatus 172 does not, however, include the intermediate anchoring devices 46 that are located between each of the electrodes 24 in the tissue cooling apparatus 26. As such, the fluid transmission space 48 between the inner surface of the outer casing member 36 and the outer surface of the electrode 24 extends uninterrupted from a fluid supply line 174 to a fluid drainage tube 176. [Note arrows F.] The ends of the supply line 174 and drainage tube 176 that terminate within the outer casing 36 are secured with anchoring devices 42 and 44.

The fluid supply line 174 may be positioned on the exterior of shaft 12 and held in place with one or more anchoring devices 178, which are similar in structure to anchoring devices 42 and 44. An exterior fluid supply line may also be used in the other surgical probe embodiments illustrated herein and an internal fluid supply line, such as that illustrated in FIG. 8, may be used in place of the external supply line in the exemplary probe illustrated in FIGS. 21 and 22.

As illustrated for example in FIG. 23, the tissue cooling apparatus 172 may be used in conjunction with surgical probes, such as the surgical probe illustrated in FIGS. 6a and 6b, that have a distal section which can be manipulated into a loop. The tissue cooling apparatus 172 may also be used in conjunction with catheters such as, for example, the catheter illustrated in FIGS. 7a and 7b.

Tissue cooling may also be accomplished through the use of a tissue cooling attachment that provides fluid cooling capabilities to an existing surgical probe. The exemplary tissue cooling attachment 180 illustrated in FIGS. 24 and 26–28 includes a base member 182 and a tubular member 184 formed with slots, holes or other apertures that supports a microporous outer casing 36. The tubular member 184 should be relatively flexible (i.e. about 70A Shore) and suitable materials include nylon, polyurethane and Sanaprene. The outer casing 36 is secured onto the tubular member 184 with anchoring devices 42 and 44. The tissue cooling attachment 180 may be combined with the surgical probe 186 illustrated in FIG. 25 to form the assembly illustrated in FIG. 26. Here, the surgical probe electrodes 24 are located within the tissue cooling apparatus outer casing 36. Fluid enters the base member 182 by way of a fluid supply line 188 and then flows through the tubular member 184 and outer casing 36 to a drainage tube 190. Alternatively, the fluid supply line 188 could be directly connected to the tubular member 184.

Figure 27:
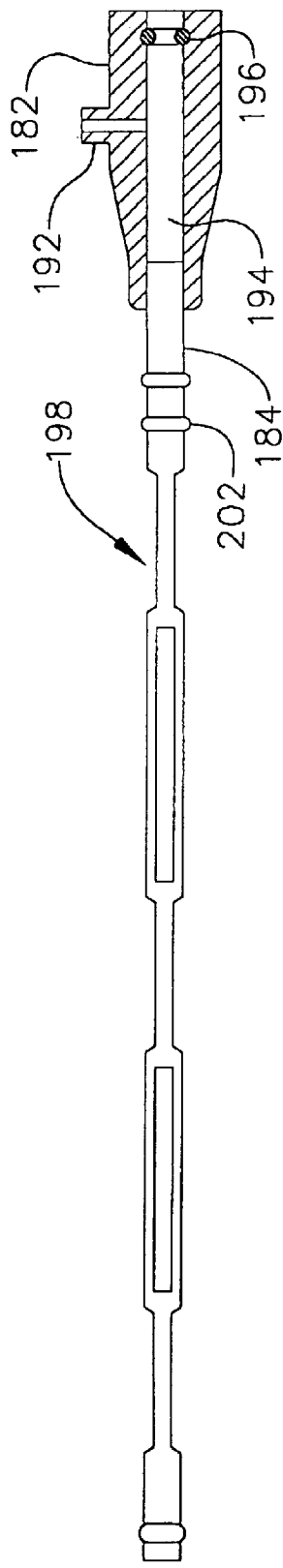
FIG. 27 is a side, partial section view of a portion of the tissue cooling attachment illustrated in FIG. 24.
Figure 28:
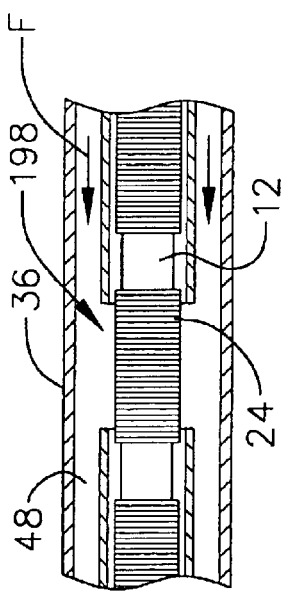
FIG. 28 is a partial section view of the combination illustrated in FIG. 26.

Referring more specifically to FIGS. 27 and 28, the base member 182, which is formed from molded plastic or other suitable materials, includes a port 192 for connection to the fluid supply line 188 and an interior lumen 194. The interior lumen 194 is connected to the port and has a slightly larger diameter than the probe shaft 12. A seal fluid-tight 196, which is positioned adjacent to the proximal end of the interior lumen 194, engages the probe shaft 12 and prevents fluid from exiting the base member 182. The seal 196, which is preferably formed from a resilient material such as latex and silicone rubber, allows the tissue cooling attachment 180 to be removably mounted on and secured to the shaft. The tubular member 184 also has a slightly larger diameter than the probe shaft. As a result, all of the fluid flows into the space between the probe shaft and the proximal end of tubular member 184. Most of the fluid exits the tubular member 184 through a series of slots 198 and fills the fluid transmission space 48, between the exterior surface of the tubular member and the interior surface of the outer casing 36, while some of the fluid remains within the tubular member 184. Fluid re-enters the tubular member 184 near its distal end by way of the distal most slot 198. From there, the fluid enters a hollow end cap 200 that is secured to the distal end of the tubular member. The end cap 200 functions as a port to which the drainage tube 190 may be connected.

In the exemplary embodiment illustrated in FIGS. 27 and 28, the tubular member 184 is provided with one or more annular protuberances 202 in the regions where the anchoring members 42 and 44 secure the microporous outer casing 36 to the tubular member. The protuberances 202 enhance the seal between the outer casing 36 and the tubular member 184.

Figure 29:
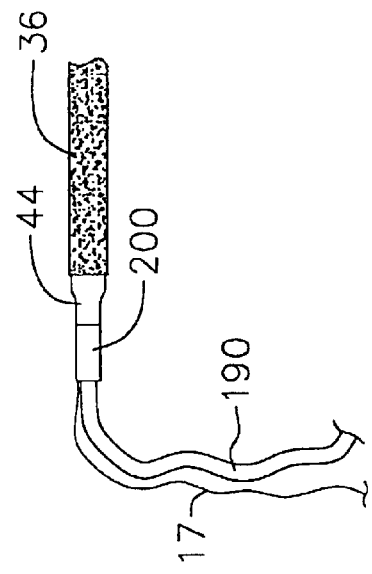
FIG. 29 is a plan view of the distal portion of a surgical probe in accordance with a preferred embodiment of a present invention.

The tissue cooling attachment 180 may also be provide with a pull wire 17 that is secured to the end cap 200 in the manner illustrated in FIG. 29. A tissue cooling attachment which includes the pull wire 17 may, for example, be used in combination with the outer member 11 illustrated in FIGS. 6b and 23. One advantage of being able to self-anchor the tissue cooling attachment 180 around a portion of the heart, such as around the pulmonary veins on the epicardial surface, is cost savings. A relatively inexpensive catheter, surgical probe, or other electrode support structure having less than a full compliment of electrodes may be inserted into a pre-positioned tissue cooling attachment 180. For example, an electrode support structure including only four distal electrodes may be inserted all the way into the pre-positioned tissue cooling attachment 180 and the first half of the lesion formed. The electrode support structure can then be partially withdrawn until the electrodes are aligned with the location of the next lesion portion and the second half of the lesion formed.

The microporous outer casing 36 in the exemplary embodiments described above with reference to FIGS. 21–29 should be no larger than 3 times the diameter of the electrodes 24 and will preferably be 1.2 to 2 times the electrode diameter. Of course, other sizes may be used if they are required by a particular application.

Finally, other methods of cooling tissue may also be employed where appropriate. Suitable methods include Joule-Thompson cooling, Peltier diode cooling (cooling using semiconductor devices that generate heat on one side while heat is removed on the other) and, in the context of wettable fluid retention elements, active vaporization.

IV. Electrodes, Temperature Sensing and Power Control

In each of the preferred embodiments, the operative element is a plurality of spaced electrodes 24 adapted to transmit RF energy. However, devices, such as ultrasonic transducers and microwave electrodes may be substituted for the electrodes.

The exemplary distal sections include seven spaced electrode elements 24. The spaced electrodes 24 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905.

Alternatively, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Given that the purpose of the electrodes is to transfer energy into the ionic fluid, as opposed to directly into tissue, the electrodes may even be replaced by a straight piece of bare wire.

The exemplary coil electrodes 24 are preferably about 4 mm to about 20 mm in length. In the preferred embodiments, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The electrodes 24 may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w and depends on parameters such as set temperature and the flow rate of the ionic fluid.

For epicardial lesion formation using the cooling apparatus 26 illustrated FIG. 1, it has been found that an 80° C. electrode temperature can be maintained with a 8 ml/min. ionic fluid flow rate when 50 w of power is supplied to each electrode for about 60 seconds. It has been found that these parameters produce lesions, both epicardial and endocardial, that are at least 11 mm wide and 8 mm deep with the devices described above. For epicardial lesion formation using the cooling apparatus 172 illustrated FIG. 21 with a outer casing having a 6 mm diameter, it has been found that an 80° C., electrode temperature can be maintained with a 8 ml/min. ionic fluid flow rate when 75 w of power is supplied to each electrode for about 60 seconds. It has been found that these parameters produce lesions, both epicardial and endocardial that are at least 20 mm wide and 18 mm deep. For purposes of comparison, a surgical probe such as that illustrated in FIG. 25, which does not include the present cooling apparatus, requires about 10 w of power to maintain an 80° C. electrode temperature and produces lesions that are about 10 mm wide and 5 mm deep. The higher power requirements for devices having the present cooling apparatus are the result of the larger surface area associated with the microporous outer casing and the convective cooling caused by the fluid flow.

As illustrated for example in FIGS. 1 and 3–5, power from a power supply and control device 96 is supplied to the electrodes 24 by conducting wires 98. The conducting wires 98 are connected to a PC board 100, which is located within the handle 14 in such a manner that it is isolated from the fluid inlet port 52. A plurality of temperature sensors (note, for example, sensors 101 in FIGS. 19 and 20), such as thermocouples or thermistors, may be located on, under, abutting the longitudinal end edges of, or in between, the electrodes 24. Preferably, the sensors will be located at or near the location where the fluid exits the respective transmission regions 48 in order to determine the temperature of the fluid at its hottest point within each transmission region. Signals from the temperature sensors are transmitted to the power supply and control device 96 by way of wires 102 that are also connected to the PC board 100. Suitable temperature sensors and power supply and control devices are disclosed in U.S. Pat. Nos. 5,456,682, 5,582,609 and 5,755,715.

In some embodiments, a reference thermocouple may also be provided. The temperature sensors may also be woven into the outer casing 36 and fluid retention elements 82, when they are formed from woven material, or embedded in the outer casing or fluid retention elements formed regenerated cellulose or other non-woven materials. Here, however, rotational movement of the tissue cooling apparatus 80 and 90 illustrated in FIGS. 10–12 should be limited to, for example, 180 degrees in order to prevent damage to the signal wires 102 connected to the temperature sensors.

V. Exemplary Lesion Locations

Surgical devices such as those illustrated above may be used to create transmural epicardial lesions to, for example, isolate the sources of focal (or ectopic) atrial fibrillation. One method of treating focal atrial fibrillation with devices such as those illustrated in FIGS. 1–10 involves the creation of transmural lesions around the pulmonary veins. Lesions may be created around the pulmonary veins individually or, alternatively, a first transmural epicardial lesion may be created around the right pulmonary vein pair and a second transmural epicardial lesion may be created around the left pulmonary vein pair. Thereafter, if needed, a linear transmural epicardial lesion may be created between the right and left pulmonary vein pairs. A linear transmural lesion that extends from the epicardial lesion to the left atrial appendage may also be formed. Alternatively, a single lesion may be formed around all four of the pulmonary veins.

The surgical devices described above may also be urged through tissue planes (i.e. the space between fascia material and a particular organ) to properly position the device prior to the actuation of the operative elements. Such a procedure is referred to as blunt dissection.

Access to the heart may be obtained via a thoracotomy, thoracostomy or median sternotomy. Ports may also be provided for cameras and other instruments.

With respect to lesions formed during open heart surgery, one exemplary lesion would extend from the incision used to gain access to the heart to the mitral valve annulus or some other anatomical barrier to reduce the potential for reentrant propagation around the incision. Lesions around the pulmonary veins may also be created.

Loops catheter-based procedures may be used to create a wide variety of lesions, as is well known in the art. A left atrial lesion used to help cure atrial fibrillation, for example, would originate on the roof of the left atrium, bisects the pulmonary veins left to right and extends posteriorly to the mitral annulus. Additional details concerning lesions that can be formed with loop catheters may be found in aforementioned U.S. Pat. No. 6,048,329.

Although the present inventions have been described in terms of the preferred embodiments above, numerous modifications and/or additions to the above-described preferred embodiments would be readily apparent to one skilled in the art. For example, the scope of the inventions includes any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A surgical probe for use with tissue, comprising:
   a shaft defining a distal portion and a proximal portion;
   a plurality of energy transmission devices supported on the distal portion of the shaft;
   a tissue cooling apparatus supported on the shaft including an outer member positioned about the plurality of energy transmission devices such that a continuous fluid transmission space is defined therebetween having an inlet and an outlet; and
   a drainage tube, extending distally from the distal portion of the shaft, that conveys fluid passing through the fluid transmission space outlet away from the tissue.

2. A surgical probe as claimed in claim 1, wherein the shaft comprises a relatively short shaft.

3. A surgical device as claimed in claim 2, wherein at least a portion of the relatively short shaft is malleable.

4. A surgical device as claimed in claim 1, wherein the plurality of energy transmission devices comprises a plurality of electrodes.

5. A surgical probe as claimed in claim 1, wherein the tissue cooling apparatus comprises a porous structure.

6. A surgical probe as claimed in claim 5, wherein the porous structure comprises a microporous structure.

7. A surgical probe as claimed in claim 1, wherein the fluid transmission space defines a substantially constant cross-sectional area between the inlet and the outlet.

8. A surgical probe as claimed in claim 1, wherein the fluid transmission space defines a substantially annular shape.

9. A surgical probe as claimed in claim 1, wherein the fluid transmission space is located radially outwardly of the energy transmission devices.

10. A surgical probe as claimed in claim 1, wherein the fluid transmission space is located between the tissue cooling apparatus and the energy transmission devices.

11. A surgical probe as claimed in claim 1, wherein the fluid transmission space surrounds the energy transmission devices.

12. A surgical probe as claimed in claim 1, wherein the energy transmission devices each define a diameter and the tissue cooling apparatus defines a diameter that is no more than about 3 times the diameter of the energy transmission devices.

13. A surgical probe as claimed in claim 12, wherein the tissue cooling apparatus defines a diameter that is about 1.2 to 2 times the diameter of the energy transmission devices.

14. A surgical probe as claimed in claim 1, wherein the plurality of energy transmission devices comprises a plurality of flexible energy transmission devices.

15. A surgical probe as claimed in claim 14, wherein the plurality of energy transmission devices comprises a plurality of coil electrodes.

16. A surgical probe, comprising:
a shaft defining a distal end and a proximal end;
a plurality of energy transmission devices supported on the shaft;
a tissue cooling apparatus supported on the shaft including an outer member positioned about the plurality of energy transmission devices such that a continuous fluid transmission space is defined therebetween having an inlet and an outlet;
a drainage tube that conveys fluid passing through the fluid transmission space outlet away from the tissue; and
a fluid supply line associated with the inlet and supported on the exterior of the shaft at the inlet.

17. A surgical probe for use with tissue, comprising:
a shaft defining a distal end and a proximal end;
a plurality of energy transmission devices supported on the shaft; and
a tissue cooling apparatus supported on the shaft including an outer member, configured to permit ionic transfer while substantially preventing fluid perfusion therethrough, positioned about the plurality of energy transmission devices such that a continuous fluid transmission space is defined therebetween having an inlet and an outlet.

18. A surgical probe as claimed in claim 17, wherein the outer member comprises a microporous structure.

19. A surgical probe as claimed in claim 17, wherein the fluid transmission space defines a substantially constant cross-sectional area between the inlet and the outlet.

20. A surgical probe as claimed in claim 17, further comprising:
a fluid supply line associated with the inlet.

21. A surgical probe as claimed in claim 17, wherein the fluid transmission space is located radially outwardly of the energy transmission devices.

22. A surgical probe as claimed in claim 17, wherein the fluid transmission space is located between the tissue cooling apparatus and the energy transmission devices.

23. A surgical probe as claimed in claim 17, wherein the fluid transmission space surrounds the energy transmission devices.

24. A surgical probe as claimed in claim 17, wherein the energy transmission devices each define a diameter and the tissue cooling apparatus defines a diameter that is no more than about 3 times the diameter of the energy transmission devices.

25. A surgical probe as claimed in claim 17, wherein the plurality of energy transmission devices comprises a plurality of flexible energy transmission devices.

26. A surgical probe as claimed in claim 25, wherein the plurality of energy transmission devices comprises a plurality of coil electrodes.

27. A surgical probe as claimed in claim 17, wherein the shaft comprises a relatively short shaft.

28. A surgical probe as claimed in claim 17, wherein the plurality of energy transmission devices comprises a plurality of electrodes.

29. A surgical probe as claimed in claim 17, wherein the energy transmission devices are located within the outer member.

30. A surgical probe, comprising:
a shaft defining an exterior, a distal end and a proximal end;
a plurality of energy transmission devices supported on the shaft; and
a tissue cooling apparatus, fixedly secured around the exterior of the shaft, including an outer member positioned about the plurality of energy transmission devices such that a continuous fluid transmission space having an inlet and an outlet is defined between the tissue cooling apparatus and the exterior of the shaft.

31. A surgical probe as claimed in claim 30, wherein the shaft comprises a relatively short shaft.

32. A surgical probe as claimed in claim 30, wherein the plurality of energy transmission devices comprises a plurality of electrodes.

33. A surgical probe as claimed in claim 30, wherein the plurality of energy transmission devices comprises a plurality of flexible energy transmission devices.

34. A surgical probe as claimed in claim 33, wherein the plurality of energy transmission devices comprises a plurality of coil electrodes.

35. A surgical probe as claimed in claim 30, wherein the outer member comprises a microporous structure.

36. A surgical probe as claimed in claim 30, wherein the fluid transmission space defines a substantially constant cross-sectional area between the inlet and the outlet.

37. A surgical probe as claimed in claim 30, further comprising:
a fluid supply line associated with the inlet.

38. A surgical probe as claimed in claim 30, wherein the energy transmission devices each define a diameter and the tissue cooling apparatus defines a diameter that is no more than about 3 times the diameter of the energy transmission devices.

39. A surgical probe as claimed in claim 30, wherein the energy transmission devices are located within the outer member.

* * * * *